United States Patent [19]

Fujii et al.

[11] 4,416,875

[45] Nov. 22, 1983

[54] ESTER DERIVATIVES OF DEOXYFLUOROURIDINE

[75] Inventors: Setsuro Fujii, Toyonaka; Bompei Yasui, Ikoma; Mitsuo Nakamura, Kyoto; Tomohisa Miyamoto, Settsu; Kazuko Ando, Hirakata; Iwao Hashimoto, Osaka; Yoneichi Sawai, Kadoma; Naoki Umeda, Osaka; Masahiro Kawasaki, Kashihara, all of Japan

[73] Assignee: Funai Yakuhin Kogyo Kabushiki Kaisha, Osaka, Japan

[21] Appl. No.: 290,420

[22] Filed: Aug. 6, 1981

[30] Foreign Application Priority Data

Aug. 13, 1980 [JP] Japan .................................. 55-112102

[51] Int. Cl.³ ....................... A61K 31/70; C07H 19/08
[52] U.S. Cl. ......................................... 424/180; 536/23
[58] Field of Search .......................... 536/23; 424/180

[56] References Cited

U.S. PATENT DOCUMENTS 3,853,845 12/1974 Rousseau et al. ..................... 536/23

FOREIGN PATENT DOCUMENTS 9882 4/1980 European Pat. Off. .
2025401 1/1980 United Kingdom .

OTHER PUBLICATIONS

Holland et al., *Cancer Medicine*, pp. 675–675 (1973).
Laurence et al., *Evaluation of Drug Activities: Pharmacometrics*, vol. 2, pp. 842 (1964).
Siegler et al., *Animal and Clinical, Pharmacologic Techniques in Drug Evaluation*, vol. 2, p. 834, p. 830 (1967).
Oslo et al., *The United States Dispensatory*, 27th Ed., pp. 377–378, 527–528 (1973).
Baker et al., *Physicians' Desk Reference*, 32nd Ed., p. 1387 (1978).
Oslo, *Remington's Pharmaceutical Sciences*, 16th Ed., pp. 1081–1082, Chapter 62 (1980).
Nodine et al., *Animal and Clinical, Pharmacologic Techniques in Drug Evaluation*, p. 632 (1964).
Dukes, *Side Effects of Drugs Annual I*, p. 336 (1977).
Carter et al., *New Drugs in Cancer Chemotherapy*, pp. 1–2 (1981).
Halnan, *Treatment of Cancer*, p. 80 (1982).
Hoshi et al., *Farumashia*, vol. 9, No. 7, pp. 464–468 (1973) and English Translation of pertinent portions.
Grollman et al., *Pharmacology and Therapeutics*, pp. 669–670 (1970).

Primary Examiner—Blondel Hazel
Attorney, Agent, or Firm—Birch, Stewart, Kolasch & Birch

[57] ABSTRACT

New ester derivatives of deoxyfluorouridine of the general formula:

wherein R and $R^{40}$, may be identical or different, and may be hydrogen, halogen or methyl and n is 3 or 4. These derivatives are prepared by acylating a 2'-deoxy-3',5'-di-O-alkylcarbonyl-5-fluorouridine with corresponding benzoyl halides and are useful as active ingredients for anti-tumor agents, especially for oral administeration.

13 Claims, No Drawings

ESTER DERIVATIVES OF DEOXYFLUOROURIDINE

BACKGROUND AND SUMMARY OF THE INVENTION

The present invention relates to new ester derivatives of deoxyfluorouridine of the general formula:

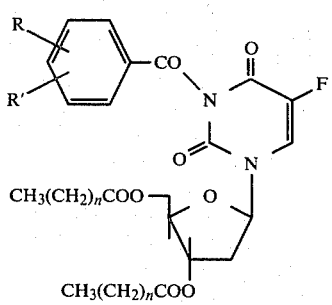
(I)

wherein R and R', which may be identical or different, each stands for a hydrogen or halogen atom or methyl group and n stands for 3 or 4. The present invention further relates to a process for the preparation of the ester derivatives and anti-tumor agents containing the ester derivatives as an active ingredient.

2'-Deoxy-5-fluorouridine (referred to hereinafter as FUDR) has been used as an anti-tumor agent but this compound is exceptionally high in toxicity for use as a medication and thus has a narrow safety region. In addition, this compound has considerable limitations in actual therapeutic applications since the mode of administering this compound is limited only to intraarterial injection, or in other words, this compound cannot be administered orally [Physicians' Desk Reference, p. 1387 (1978)]. 2'-Deoxy-3',5'-di-O-acetyl-5-fluorouridine (referred to hereinafter simply as acetyl-FUDR) is also known as one of the FUDR derivatives. However, this compound is evaluated as being almost equivalent in anti-tumor activity to FUDR and rather poor in effectiveness [Biochem. Pharmacology, 14, 1605 et seq., (1965); Cancer Research, 23, 420 et seq. (1963)].

3',5'-Dialkyl esters of FUDR are also reported as derivatives of FUDR [Biochem. Pharmacology, 14, 1605-1619 (1965), ibid. 15, 627-644 (1966)]. However, no compound was found which was satisfactory with respect to anti-tumor activity and toxicity levels. It was reported by C. Heidelberger et al that the nitrogen atom in the 3-position of the pyrimidine nucleus of FUDR should not be substituted for anti-tumor activity [Cancer Research, 30, 1555-6, (1970)]. It has been found unexpectedly that compounds having a specific aroyl group as a substituent on the nitrogen atom in the 3-position of the pyrimidine nucleus of FUDR, for example, 3-(3-methylbenzoyl)-2'-deoxy-3',5'-di-O-acetyl-5-fluorouridine etc., have a superior anti-tumor activity (Japanese unexamined patent publication No. 35057/1980). Some derivatives substituted on the 3-position of the pyrimidine of FUDR, for example, 3-(3-methylbenzoyl)-2'-deoxy-5-fluorouridine etc., are also known (Japanese unexamined patent publication No. 163586/1979). However, improvement in anti-tumor activity in such FUDR compounds is desirable.

Recently, reported FUDR and acetyl-FUDR derivatives have included compounds wherein the hydrogen atom bonded to the nitrogen atom at the 3-position on the uracil ring is substituted by a specific aroyl group (UK Patent Appln. No. 2,025,401 published on Jan. 23, 1980 and European Patent Appln. No. 9,882 published on Apr. 16, 1980). However, further enhancement in anti-tumor activity is desired also in these compounds. Thus, there is a great demand for developing new FUDR derivatives which possess strong anti-tumor activity with weak toxicity and are suitable for oral administration without the necessity of troublesome intraarterial or intravenous injection.

DETAILED DESCRIPTION OF THE INVENTION

As a result of extensive research made on a variety of FUDR derivatives for enhancing their anti-tumor activity and concurrently reducing their toxicity, it has now been surprisingly found that the new compounds of the general formula (I) are superior in anti-tumor activity to the known similar compounds. The present invention has been accomplished on the basis of the above finding.

In formula (I) above, the halogen atom can be chlorine, bromine, fluorine or iodine. For example, one or two of the halogen atoms mentioned above and a methyl group may be substituted on the phenyl nucleus in the formula (I).

The new compounds of the general formula (I) of the present invention are prepared, for example, by reacting a 2'-deoxy-3',5'-di-O-alkylcarbonyl-5-fluorouridine of the general formula:

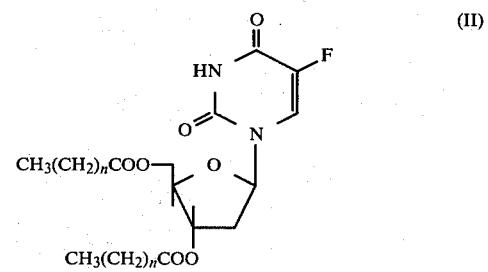
(II)

wherein n has same meaning as given above, with a benzoyl halide of the general formula:

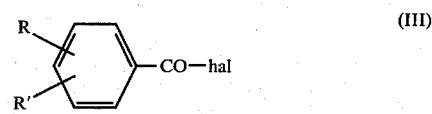
(III)

wherein hal stands for a halogen atom and R and R' have the same meaning as given above.

As the benzoyl halide starting material, the use of the corresponding chloride or bromide is preferable.

The benzoyl halide of the general formula (III) is preferably used in an amount of 1-3 molar proportion for the 2'-deoxy-3',5'-di-O-alkylcarbonyl-5-fluorouridine.

As a rule, the reaction is preferably carried out in an organic solvent. Illustrative of the preferable organic solvents are aprotic solvents such as diethyl ether, dioxane, chloroform, ethyl acetate, acetonitrile, pyridine, dimethylformamide and dimethylsulfoxide.

The reaction is carried out normally in the presence of an organic base, particularly an aromatic amine such as pyridine, trialkylamines or N,N-dialkylanilines.

The organic base is used usually in an amount of 1–5 moles per mole of the benzoyl halide. As the organic bases per se may be used as the reaction medium, an excess amount of the organic base may be used.

The reaction can be carried out within a wide range of reaction temperatures, for example, under ice cooling or at a temperature up to the boiling point of the reaction solvent utilized. As a rule, the reaction time is preferably within a period from 30 minutes to a few hours.

After completion of the reaction, the end product can be obtained by subjecting the reaction mixture directly to concentration under reduced pressure or by first filtering the reaction mixture and then concentrating the filtrate under the reduced pressure, and finally recrystallizing the resultant residue or subjecting the residue to chromatography. When the end product is isolated as a viscous oily substance, it can be obtained as a solid form by dissolving the oily substance in a small amount of dimethylsulfoxide and pouring the solution slowly into water under agitation.

The pharmacological tests for the thus obtained compounds of the present invention were carried out as follows:

I. Methods for testing (a) Pharmacological tests for measuring anti-tumor activity:

About 10,000,000 tumor cells of Sarcoma 180 (successively incubated for several generations in the peritoneal cavity of a male mouse of ICR strain) were transplanted subcutaneously into the inguinal region of 5 week-aged male mice of ICR strain. After the lapse of 24 hours, administration of the compounds of the present invention was started. The administration of the compounds of the invention was forcibly made orally once a day for 7 days. The body weight of each testing animal was measured every day just before the administration. The compounds of the invention dissolved in polyethylene glycol 400 were administered to each testing animal while polyethylene glycol 400 alone as placebo was administered to a control group of the animals. In each case, the same volume of 0.1 ml/10 g (body weight) was administered to each animal. Although the exact doses of the compounds of the invention was varied depending on the particular compounds utilized, the doses were approximately within a range of from 0.5 mg/kg to 120 mg/kg. The doses were graded into 3–12 ranks for each testing compound. At each rank, the compound of the invention was administered to a group consisting of 6 mice while the placebo was administered to a control group consisting of 18 mice.

On the 8th day of the transplantation of the tumor cells, each mouse was put to death by bleeding under ether anesthesia. After the tumor tissue was excised, its weight was immediately measured and recorded. An average value of tumor weights in the treated group (referred to as T) for each test compound at for each dose and an average value of tumor weights in the control group (referred to as C) were respectively calculated, to estimate a dose corresponding to T/C value of 0.70 or 0.50 for each test compound.

Concerning evaluation of the anti-tumor activity, a T/C value within the range of 0.70–0.51 is regarded to be moderately effective, while a value of less than 0.50 is regarded to be effective [Ohyo-Yakuri, 7, 1277–1292 (1973)]. Accordingly, the anti-tumor activity becomes stronger as the T/C value becomes smaller.

(b) Test for measuring toxicity:

Judging from the effects achieved by the compounds of the present invention, toxicity values were measured according to the following method, taking accumulative toxicity into consideration.

Groups of 5 week old male mice of ICR strain were used for this test, each group consisting of 10 animals. Test compounds were forcibly administered orally once a day for 7 days. The body weight of each animal was measured every day just before the administration. The compounds of the present invention dissolved in polyethylene glycol 400 were administered to each testing animal in the same volume of 0.1 ml/10 g (body weight). Although the exact doses of the compound of the invention varied depending on the particular compounds utilized, the doses were approximately within a range from 2 mg/kg to 300 mg/kg. The doses were graded into 5 ranks for each testing compound. At each rank, the compound of the invention was administered to each group. On the 14th day after the completion of administration, the survival and death of the tested animals were judged and $LD_{10}$ values were calculated according to the Litchfield-Wilcoxon method.

II. Results of the Tests:

The results of the above Tests (a) and (b) and the therapeutic indices calculated therefrom are shown in Table 1. The therapeutic indices were calculated according to the following equation:

Therapeutic index = $LD_{10}$ value ÷ T/C 0.50 value

TABLE 1

| Compound administered | | | Value indicating T/C 0.50 | $LD_{10}$ | Thera- |
|---|---|---|---|---|---|
| In General Formula, R and R' | | n | (mg/Kg) | (mg/Kg) | peutic index |
| Compounds of the present invention | H | 3 | 1.0 | 8.6 | 8.60 |
| | 2-Methyl | " | 2.0 | 9.5 | 4.75 |
| | 3-Methyl | " | 3.6 | 8.1 | 2.25 |
| | 3,5-Dimethyl | " | 6.0 | 22 | 3.67 |
| | 3-Fluoro | " | 13 | 30 | 2.31 |
| | 2-Chloro | " | 13 | 33 | 2.54 |
| | 2,4-Dichloro | " | 14 | 31 | 2.21 |
| | H | 4 | 1.0 | 0.4 | 0.40 |
| | 2-Methyl | " | 5.0 | 13 | 2.20 |
| | 3-Methyl | " | 5.7 | 16 | 2.81 |
| | 4-Methyl | " | 5.3 | 12 | 2.26 |
| | 2,4-Dimethyl | " | 6.3 | 16 | 2.54 |
| | 3-Fluoro | " | 5.8 | 17 | 2.93 |
| | 4-Fluoro | " | 6.1 | 18 | 2.95 |
| | 3-Chloro | " | 8.6 | 23 | 2.67 |
| | 4-Bromo | " | 10 | 26 | 2.60 |
| | 3,5-Dichloro | " | 13 | 37 | 2.85 |
| *Known Compounds | A | | 28 | 28 | 1.00 |
| | B | | 9.0 | 19 | 2.11 |
| | C | | 62 | 91 | 1.50 |
| | D | | 41 | 89 | 2.17 |
| | E | | 70 | 61 | 0.87 |
| | F | | 37 | 43 | 1.16 |
| | G | | 67 | 63 | 0.94 |

*The same tests as indicated in paragraphs (a) and (b) were conducted, using the following known similar compounds:
A: 2'-Deoxy-3',5'-di-O—n-pentanoyl-5-fluorouridine
B: 2'-Deoxy-3',5'-di-O—n-hexanoyl-5-fluorouridine
C: 3-(3-methylbenzoyl)-2'-deoxy-5-fluorouridine
D: 3-(3-methylbenzoyl)-2'-deoxy-3',5'-di-O—acetyl-5-fluorouridine
E: 3-(3,4-methylenedioxybenzoyl)-2'-deoxy-5-fluorouridine
F: 3-(3,4-methylenedioxybenzoyl)-2'-deoxy-3',5'-di-O—acetyl-5-fluorouridine
G: 5-Fluorouracil As is evident from the results shown in Table 1, the compounds of the present invention exhibit strong anti-tumor activity in comparison with the known similar compounds.

In clinical chemotherapy, the compounds of the present invention are preferably administered in a daily dose of 1–600 mg. As a mode of administration, oral administration is preferably applied to the compounds of the present invention but parenteral administration such as intravenous injection or intrarectal medical by means of a suppository is also applicable.

As pharmaceutical preparations suitable for oral administration, tablets, capsules (hard capsules and soft capsules), liquids and grandules, each unit-containing 0.5–100 mg of the compound of the invention as the active ingredient, can be utilized. These preparations may contain, in addition to the active ingredient, other conventional auxiliary components such as milk sugar, corn starch, potato starch, various cane sugar esters of fatty acids, microcrystalline cellulose and polyethylene glycol 4000 as excipients; acacia, gelatine, hydroxypropylcellulose and potato starch as binders; magnesium stearate and talc as lubricants; and carboxymethylcellulose calcium, potato starch and corn starch as disintegrating agents. Usual solubilizing agents and suspending agents may also be contained in the preparations, with polyethylene glycol 200–600 being the particular liquid preferred. Examples of a base for suppositories include glycerin, cacao butter, glycerogelatine, polyethylene glycol, and the like.

Besides the above mentioned additives, materials normally used as carriers for pharmaceutical preparations may also be included with the anti-tumor agents of the present invention.

SOFT CAPSULE PREPARATIONS

The following is a soft capsule preparation:

| Recipe: | |
|---|---|
| the compound of the present invention | 50 mg |
| polyethylene glycol 400 | 250 mg |
| propylene glycol | 10 mg |
| bleached beeswax | 10 mg |
| total | 320 mg |

The following compounds can be used as the compound of the present invention for the above recipe:
- 3-(2-methylbenzoyl)-2'-deoxy-3',5'-di-O-n-pentanoyl-5-fluorouridine
- 3-(3-methylbenzoyl)-2'-deoxy-3',5'-di-O-n-hexanoyl-5-fluorouridine
- 3-benzoyl-2'-deoxy-3',5'-di-O-n-hexanoyl-5-fluorouridine Capsules are formed according to a conventional method so that each capsule may contain the above dose of ingredients. As a rule, 3–9 capsules per day can be administered orally to adult patients.

The present invention will now be illustrated in more detail by way of the following examples which are given as being exemplary of the present invention and accordingly should not be considered in any way as limiting the scope thereof.

EXAMPLE 1

To a solution of 7.0 g of 2'-deoxy-3',5'-di-O-n-pentanoyl-5-fluorouridine in 50 ml of dry dioxane were added 3.7 ml of triethylamine and 2.7 g of benzoyl chloride. The mixture was subjected to reaction at room temperature for 2 hours and then at 60° C. for 30 minutes. The reaction liquid was cooled and then concentrated under reduced pressure. The residue was dissolved in ethyl acetate and the solution was washed with a 0.1-N aqueous solution of caustic soda and then with a saturated aqueous solution of edible salt and dried with anhydrous sodium sulfate. The solvent was removed by distillation under reduced pressure and the residue was purified by column chromatography on silica gel (elution solvent: chloroform). The resultant oily substance was dissolved in about 80 ml of ethanol and the solution was treated with active carbon. The ethanol was distilled off under reduced pressure and the residue was again purified by column chromatography on silica gel (elution solvent: chloroform). The resultant purified oily substance was dried at room temperature under reduced pressure whereby 7.9 g (90%) of 3-benzoyl-2'-deoxy-3',5'-di-O-n-pentanoyl-5-fluorouridine were obtained as an oily substance.

UV ($\lambda_{max}^{EtOH}$, nm): 253.

NMR $\delta$(ppm, CDCl$_3$):

Uridine moiety: 7.79 (d, H$_6$), 6.26 (broad-t, H$_1'$), near 2.4 (m, H$_2'$), 5.16–5.32 (m, H$_3'$), 4.20–4.56 (m, H$_4'$, H$_5'$), 2.08–2.64 (m, 2×COCH$_2$), 1.16–1.84 (m, 4×CH$_2$), 0.80–1.08 (m, 2×CH$_3$)

Benzoyl moiety: 7.36–8.02 (m, aromatic H)

Elementary analysis (as C$_{26}$H$_{31}$FN$_2$O$_8$): Calc. (%): C 60.22; H 6.03; N 5.40. Found (%): C 60.33; H 6.08; N 5.55.

EXAMPLES 2–6

In the same manner as described in Example 1, the following ester derivatives of deoxyfluorouridine were prepared. The structures, yields and physical characteristics of the end products obtained are shown in Table 2.

TABLE 2

| Example No | In General Formula (I), R, R' (n) | Yield (%) Nature | Elementary Analysis Empirical Formula Calc. (%): C, H, N Found (%): C, H, N | UV $\lambda_{max}^{EtOH}$ (nm) | NMR (CDCl$_3$) $\delta$ (ppm) Uridine moiety | | | | Benzoyl moiety |
|---|---|---|---|---|---|---|---|---|---|
| 2 | H (4) | 82 Oily subst. | C$_{25}$H$_{35}$FN$_2$O$_8$ 61.53 6.45 5.12 61.71 6.54 5.29 | 253 | 7.79 near 2.4 4.20–4.57 1.19–1.88 | (d, H$_6$) (m, H$_2'$) (m, H$_4'$, H$_5'$) (m, 6 × CH$_2$) | 6.26 5.16–5.32 2.07–2.65 0.78–1.08 | (broad-t, H$_1'$) (m, H$_3'$) (m, 2 × COCH$_2$) (m, 2 × CH$_3$) | 7.40–8.04 (m, aromatic H) |
| 3 | 2-methyl (3) | 79 Oily subst. | C$_{27}$H$_{33}$FN$_2$O$_8$ 60.89 6.25 5.26 60.72 6.34 5.34 | 255 | 7.76 near 2.4 4.20–4.56 1.16–1.84 | (d, H$_6$) (m, H$_2'$) (m, H$_4'$, H$_5'$) (m, 4 × CH$_2$) | 6.26 5.15–5.32 2.04–2.66 0.80–1.08 | (broad-t, H$_1'$) (m, H$_3'$) (m, 2 × COCH$_2$) (m, 2 × CH$_3$) | 7.16–7.68 (m, aromatic H) 2.68 (S, CH$_3$) |
| 4 | 3-fluoro (3) | 76 Oily subst. | C$_{26}$H$_{30}$F$_2$N$_2$O$_8$ 58.20 5.64 5.22 58.01 5.74 5.31 | 252 | 7.79 near 2.4 4.20–4.56 1.15–1.82 | (d, H$_6$) (m, H$_2'$) (m, H$_4'$, H$_5'$) (m, 4 × CH$_2$) | 6.25 5.16–5.32 2.05–2.66 0.79–1.05 | (broad-t, H$_1'$) (m, H$_3'$) (m, 2 × COCH$_2$) (m, 2 × CH$_3$) | 7.24–7.88 (m, aromatic H) |
| 5 | 3-methyl (4) | 83 Oily subst. | C$_{29}$H$_{37}$FN$_2$O$_8$ 62.13 6.65 5.00 62.08 6.78 4.94 | 258 | 7.76 near 2.4 4.20–4.50 | (d, H$_6$) (m, H$_2'$) (m, H$_4'$, H$_5'$) | 6.25 5.12–5.30 2.04–2.66 | (broad-t, H$_1'$) (m, H$_3'$) (m, 2 × COCH$_2$) | 7.61–7.80 (m, H$_2$, H$_6$) 7.24–7.54 |

TABLE 2-continued

| Example No | In General Formula (I), R, R' (n) | Yield (%) Nature | Elementary Analysis Empirical Formula Calc. (%): C, H, N Found (%): C, H, N | UV $\lambda_{max}^{EtOH}$ (nm) | NMR (CDCl$_3$) δ (ppm) Uridine moiety | | | Benzoyl moiety |
| --- | --- | --- | --- | --- | --- | --- | --- | --- |
| 6 | 4-methyl (4) | 87 Oily subst. | C$_{29}$H$_{37}$FN$_2$O$_8$ 62.13  6.65  5.00 62.30  6.68  5.00 | 264 | 1.12–1.82 7.77 near 2.4 4.16–4.52 1.16–1.30 | (m, 6 × CH$_2$) (d, H$_6$) (m, H'$_2$) (m, H'$_4$, H'$_5$) (m, 6 × CH$_2$) | 0.77–1.02  (m, 2 × CH$_3$) 6.22  (broad-t, H'$_1$) 5.10–5.28  (m, H'$_3$) 2.00–2.64  (m, 2 × COCH$_2$) 0.76–1.00  (m, 2 × CH$_3$) | (m, H$_4$, H$_5$) 2.40 (S, CH$_3$) 7.70 (d, H$_2$, H$_6$) 7.24 (d, H$_3$, H$_5$) 2.40 (S, CH$_3$) |

EXAMPLE 7

To a solution of 7.0 g of 2'-deoxy-3',5'-di-O-n-pentanoyl-5-fluorouridine in 50 ml of dry dioxane were added 4.0 ml of triethylamine and 3.4 g of 3-methylbenzoyl chloride. The mixture was subjected to reaction at room temperature for 5 hours and the reaction liquid was concentrated under reduced pressure. The residue was dissolved in ethyl acetate and the solution was washed with a 0.1-N aqueous solution of caustic soda and then with a saturated aqueous solution of edible salt and dried with anhyrous sodium sulfate. The solvent was removed by distillation under reduced pressure and the residue was purified twice by column chromatography on silica gel (elution solvent: chloroform). The resultant purified oily substance was dried at room temperature under reduced pressure whereby 6.0 g (66%) of 3-(3-methylbenzoyl)-2'-deoxy-3',5'-di-O-n-pentanoyl-5-fluorouridine were obtained as an oily substance.

UV ($\lambda_{max}^{EtOH}$, nm): 258.

NMR δ(ppm, CDCl$_3$):

Uridine moiety: 7.76 (d, H$_6$), 6.26 (broad-t, H$_1$'), near 2.4 (m, H$_2$'), 5.16–5.32 (m, H$_3$'), 4.20–4.56 (m H$_4$', H$_5$'), 2.05–2.67 (m, 2×COCH$_2$), 1.16–1.84 (m, 4×CH$_2$), 0.80–1.06 (m, 2×CH$_3$).

Benzoyl moiety: 7.26–7.56 (m, H$_4$, H$_5$), 7.64–7.88 (m, H$_2$, H$_6$), 2.38 (s, CH$_3$).

Elementary analysis (as C$_{27}$H$_{33}$FN$_2$O$_8$): Calc. (%): C 60.89; H 6.25; N 5.26. Found (%): C 60.87; H 6.46; N 5.30.

EXAMPLE 8

Using benzoyl chloride in the same manner as described in Example 7, 7.4 g (84%) of 3-benzoyl-2'-deoxy-3',5'-di-O-n-pentanoyl-5-fluorouridine were obtained as an oily substance. The physical characteristics of this substance were identical with those of the oily substance obtained in Example 1.

EXAMPLE 9

To a solution of 7.5 g of 2'-deoxy-3',5'-di-O-n-hexanoyl-5-fluorouridine in 50 ml of dry dioxane were added 10.7 ml of triethylamine and 3.6 g of benzoyl chloride. The mixture was subjected to reaction at room temperature for 4 hours. The reaction liquid was concentrated under reduced pressure and the residue was dissolved in ethyl acetate. The solution was washed with a 0.1-N aqueous solution of caustic soda and then with a saturated aqueous solution of edible salt and dried with anhydrous sodium sulfate. The solvent was removed by distillation under reduced pressure and the residue was purified twice by column chromatography on silica gel (elution solvent: chloroform). The resultant purified oily substance was dried at room temperature under reduced pressure whereby 8.1 g (87%) of 3-benzoyl-2'-deoxy-3',5'-di-O-n-hexanoyl-5-fluorouridine were obtained as an oily substance. The physical characteristics of this substance were identical with those of the oily substance obtained in Example 2.

EXAMPLE 10

To a solution of 7.0 g of 2'-deoxy-3',5'-di-O-n-pentanoyl-5-fluorouridine in 50 ml of dry dioxane were added 3.7 ml of triethylamine and 3.4 g of 3,5-dimethylbenzoyl chloride. The mixture was subjected to reaction at room temperature for one hour and then at 60° C. for 30 minutes. The reaction liquid was cooled and then treated in the same manner as described in Example 1 whereby 6.6 g (71%) of 3-(3,5-dimethylbenzoyl)-2'-deoxy-3',5'-di-O-n-pentanoyl-5-fluorouridine were obtained as an oily substance.

UV ($\lambda_{max}^{EtOH}$, nm): 263.

NMR δ(ppm, CDCl$_3$):

Uridine moiety: 7.79 (d, H$_6$), 6.28 (broad-T, H$_1$'), near 2.4 (m, H$_2$'), 5.16–5.32 (m, H$_3$'), 4.20–4.46 (m, H$_4$', H$_5$'), 2.14–2.52 (m, 2×COCH$_2$), 1.16–1.84 (m, 4×CH$_2$), 0.82–1.04 (m, 2×CH$_3$).

Benzoyl moiety: 7.54 (s, H$_2$, H$_6$), 7.30 (s, H$_4$), 2.34 (s, 2×CH$_3$).

Elementary analysis (as C$_{28}$H$_{35}$FN$_2$O$_8$): Calc. (%): C 61.53; H 6.45; N 5.12. Found (%): C 61.69; H 6.63; N 5.31.

EXAMPLE 11

Using 3-methylbenzoyl chloride in the same manner as described in Example 10, 6.6 g (73%) of 3-(3-methylbenzoyl)-2'-deoxy-3',5'-di-O-n-pentanoyl-5-fluorouridine were obtained as an oily substance. The physical characteristics of this substance were identical with those of the oily substance obtained in Example 7.

EXAMPLE 12

To a solution of 7.5 g of 2'-deoxy-3',5'-di-O-n-hexanoyl-5-fluorouridine in 50 ml of dry dioxane were added 3.7 ml of triethylamine and 3.2 g of 3-fluorobenzoyl chloride. The mixture was subjected to reaction at room temperature for 4 hours and then at 60° C. for 30 minutes. The reaction liquid was cooled and then treated in the same manner as described in Example 7 whereby 7.0 g (73%) of 3-(3-fluorobenzoyl)-2'-deoxy-3',5'-di-O-n-hexanoyl-5-fluorouridine were obtained as an oily substance.

UV ($\lambda_{max}^{EtOH}$, nm): 252.

NMR δ(ppm, CDCl$_3$):

Uridine moiety: 7.77 (d, H$_6$), 6.24 (broad-t, H$_1$'), near 2.4 (m, H$_2$'), 5.14–5.30 (m, H$_3$'), 4.20–4.56 (m H$_4$', H$_5$'), 2.04–2.68 (m, 2×COCH$_2$), 1.12–1.82 (m, 6×CH$_2$), 0.78–1.04 (m, 2×CH$_3$).

Benzoyl moiety: 7.24–7.84 (m, aromatic H).

Elementary analysis (as $C_{28}H_{34}F_2N_2O_8$): Calc. (%): C 59.57; H 6.07; N 4.96. Found (%): C 59.69; H 6.31; N 5.02.

EXAMPLES 13–20

In the same manner as described in Example 12 or in the same manner as described in that Example except that the reaction time was varied, the ester derivatives of deoxyfluorouridine as shown in Table 3 were prepared. The structures, yields and physical characteristics of the prepared derivatives are shown in Table 3.

TABLE 3

| Example No | In General Formula (1), R, R' (n) | Yield (%) (Nature) | Elementary Analysis Empirical formula Calc. (%): C, H, N Found (%): C, H, N | UV $\lambda_{max}^{EtOH}$ (nm) | NMR (CDCl$_3$) δ (ppm) Uridine moiety | NMR (CDCl$_3$) δ (ppm) Benzoyl moiety | Reaction time Room (hr) | Reaction time 60° C. (hr) |
|---|---|---|---|---|---|---|---|---|
| 13 | 2-methyl (4) | 76 (Oily subst.) | C$_{29}$H$_{37}$FN$_2$O$_8$ 62.13 6.65 5.00 61.98 6.54 5.02 | 256 | 7.75 (d, H$_6$) near 2.4 (m, H'$_2$) 4.18-4.54 (m, H$_4$, H'$_5$) 1.16-1.82 (m, 6 × CH$_2$) | 6.23 (broad-t, H'$_1$) 5.12-5.28 (m, H$_3$) 2.00-2.65 (m, 2 × COCH$_2$) 0.76-1.02 (m, 2 × CH$_3$) | 7.12-7.64 (m, aromatic H) 2.68 (S, CH$_3$) | 4 | 0.5 |
| 14 | 2,4-dimethyl (4) | 58 (Oily subst.) | C$_{30}$H$_{39}$FN$_2$O$_8$ 62.70 6.84 4.87 62.38 6.92 4.81 | 265 | 7.74 (d, H$_6$) near 2.4 (m, H'$_2$) 4.19-4.54 (m, H$_4$, H'$_5$) 1.16-1.82 (m, 6 × CH$_2$) | 6.23 (broad-t, H'$_1$) 5.14-5.29 (m, H$_3$) 2.00-2.64 (m, 2 × COCH$_2$) 0.78-1.04 (m, 2 × CH$_3$) | 7.46 (d, H$_6$) 7.14 (S, H$_3$) 7.04 (d, H$_5$) 2.66 (S, CH$_3$) 2.36 (S, CH$_3$) | 1 | 3 |
| 15 | 2-chloro (3) | 70 (Oily subst.) | C$_{26}$H$_{30}$ClFN$_2$O$_8$ 56.47 5.47 5.07 56.65 5.55 4.81 | 255 | 7.78 (d, H$_6$) near 2.4 (m, H'$_2$) 4.20-4.56 (m, H$_4$, H'$_5$) 1.12-1.81 (m, 4 × CH$_2$) | 6.23 (broad-t, H'$_1$) 5.14-5.32 (m, H$_3$) 2.04-2.68 (m, 2 × COCH$_2$) 0.80-1.03 (m, 2 × CH$_3$) | 7.90 (d, H$_6$) 7.28-7.59 (m, H$_3$, H$_4$, H$_5$) | 1 | 2 |
| 16 | 2,4-dichloro (3) | 71 (Oily subst.) | C$_{26}$H$_{29}$Cl$_2$FN$_2$O$_8$ 53.16 4.98 4.77 53.23 5.15 4.53 | 263 | 7.76 (d, H$_6$) near 2.4 (m, H'$_2$) 4.22-4.56 (m, H$_4$, H'$_5$) 1.16-1.86 (m, 4 × CH$_2$) | 6.23 (broad-t, H'$_1$) 5.15-5.30 (m, H$_3$) 2.03-2.69 (m, 2 × COCH$_2$) 0.82-1.10 (m, 2 × CH$_3$) | 7.86 (d, H$_6$) 7.22-7.54 (m, H$_3$, H$_5$) | 1 | 2 |
| 17 | 4-fluoro (4) | 59 (Oily subst.) | C$_{28}$H$_{34}$F$_2$N$_2$O$_8$ 59.57 6.07 4.96 59.42 5.00 5.03 | 256 | 7.77 (d, H$_6$) near 2.4 (m, H'$_2$) 4.20-4.56 (m, H$_4$, H'$_5$) 1.14-1.84 (m, 6 × CH$_2$) | 6.24 (broad-t, H'$_1$) 5.14-5.30 (m, H$_3$) 2.06-2.66 (m, 2 × COCH$_2$) 0.78-1.06 (m, 2 × CH$_3$) | 7.84-8.06 (m, H$_2$, H$_6$) 7.16 (t, H$_3$, H$_5$) | 1 | 2 |
| 18 | 3-chloro (4) | 68 (Oily subst.) | C$_{28}$H$_{34}$ClFN$_2$O$_8$ 57.88 5.90 4.82 57.73 5.78 4.61 | 255 | 7.80 (d, H$_6$) near 2.4 (m, H'$_2$) 4.20-4.60 (m, H$_4$, H'$_5$) 1.16-1.86 (m, 6 × CH$_2$) | 6.26 (broad-t, H'$_1$) 5.16-5.32 (m, H$_3$) 2.06-2.70 (m, 2 × COCH$_2$) 0.80-1.06 (m, 2 × CH$_3$) | 7.24-7.94 (m, aromatic H) | 1 | 1 |
| 19 | 4-Bromo (4) | 62 (Oily subst.) | C$_{28}$H$_{34}$BrFN$_2$O$_8$ 53.77 5.48 4.48 53.71 5.42 4.30 | 267 | 7.78 (d, H$_6$) near 2.4 (m, H'$_2$) 4.20-4.56 (m, H$_4$, H'$_5$) 1.14-1.84 (m, 6 × CH$_2$) | 6.23 (broad-t, H'$_1$) 5.12-5.30 (m, H$_3$) 2.04-2.68 (m, 2 × COCH$_2$) 0.76-1.04 (m, 2 × CH$_3$) | 7.52-7.84 (m, aromatic H) | 1 | 1 |
| 20 | 3,5-dichloro (4) | 73 (Oily subst.) | C$_{28}$H$_{33}$Cl$_2$FN$_2$O$_8$ 54.64 5.40 4.55 54.61 5.32 4.46 | 258 | 7.80 (d, H$_6$) near 2.4 (m, H'$_2$) 4.16-4.60 (m, H$_4$, H'$_5$) 1.16-1.84 (m, 6 × CH$_2$) | 6.24 (broad-t, H'$_1$) 5.16-5.32 (m, H$_3$) 2.08-2.70 (m, 2 × COCH$_2$) 0.80-1.06 (m, 2 × CH$_3$) | 7.72-7.86 (m, H$_2$, H$_4$) 7.60-7.72 (m, H$_4$) | 1 | 2 |

EXAMPLE 21

To a solution of 7.0 g of 2'-deoxy-3',5'-di-O-n-pentanoyl-5-fluorouridine of 50 ml of dry acetonitrile were added under ice cooling 7.8 ml of triethylamine and 2.6 g of benzoyl chloride. The mixture was subjected to reaction at room temperature for 3 hours and then at 50°–60° C. for 10 minutes. The reaction liquid was cooled and then concentrated under reduced pressure and the residue was purified twice by column chromatography on silica gel (elution solvent: chloroform). The resultant purified oily substance was dried at room temperature under reduced pressure whereby 7.0 g (79%) of 3-benzoyl-2'-deoxy-3',5'-di-O-n-pentanoyl-5-fluorouridine were obtained as an oily substance. The physical characteristics of this substance were identical with those of the oily substance obtained in Example 1.

EXAMPLE 22

To a solution of 7.5 g of 2'-deoxy-3',5'-di-O-n-hexanoyl-5-fluorouridine in 50 ml of dioxane were added 5.2 ml of triethylamine and 2.6 g of benzoyl chloride. The mixture was subjected to reaction at room temperature for 2 hours and then at 50°–60° C. for 30 minutes. The reaction liquid was cooled and filtered to remove insoluble matters. The filtrate was treated in the same manner as described in Example 21 whereby 7.1 g (76%) of 3-benzoyl-2'-deoxy-3',5'-di-O-n-hexanoyl-5-fluorouridine were obtained as an oily substance. The physical characteristics of this substance were identical with those of the oily substance obtained in Example 2.

EXAMPLE 23

Using 2-methylbenzoyl chloride in the same manner as described in Example 22, 6.8 g (75%) of 3-(2-methylbenzoyl)-2'-deoxy-3',5'-di-O-n-pentanoyl-5-fluorouridine were obtained as an oily substance. The physical characteristics of this substance were identical with those of the oily substance obtained in Example 3.

EXAMPLE 24

To a solution of 1.0 g of 2'-deoxy-3',5'-di-O-n-pentanoyl-5-fluorouridine in 10 ml of dry dioxane were added under ice cooling 0.52 ml of triethylamine and 0.54 g of benzoyl bromide. The mixture was subjected to reaction at room temperature for 15 minutes and then at 70° C. for 30 minutes. The reaction solution was washed with an aqueous solution of sodium bicarbonate and then with a saturated aqueous solution of edible salt and treated in the same manner as described in Example 7 whereby 0.75 g (60%) of 3-benzoyl-2'-deoxy-3',5'-di-O-n-pentanoyl-5-fluorouridine were obtained as an oily substance. The physical characteristics of this substance were identical with those of the oily substance obtained in Example 1.

EXAMPLE 25

To a solution of 7.5 g of 2'-deoxy-3',5'-di-O-n-hexanoyl-5-fluorouridine in 40 ml of ethyl acetate were added 4.6 ml of triethylamine and 2.7 g of 3-fluorobenzoyl chloride. The mixture was subjected to reaction at room temperature for 3 hours and then at 50°–60° C. for one hour. The reaction liquid was cooled and washed with a 0.1-N aqueous solution of the caustic soda and then with a saturated aqueous solution of edible salt and dried with anhydrous sodium sulfate. The solvent was removed by distillation and the residue was treated in the same manner as described in Example 7 whereby 6.0 g (63%) of 3-(3-fluorobenzoyl)-2'-deoxy-3',5'-di-O-n-hexanoyl-5-fluorouridine were obtained as an oily substance. The physical characteristics of this substance were identical with those of the oily substance obtained in Example 12.

EXAMPLE 26

To a solution of 7.0 g of 2'-deoxy-3',5'-di-O-n-pentanoyl-5-fluorouridine in 50 ml of dry dioxane were added 6.3 ml of triethylamine and 5.7 g of 3,5-dimethylbenzoyl chloride. The mixture was subjected to reaction at room temperature for 4 hours. The reaction liquid was treated in the same manner as described in Example 7 whereby 5.9 g (63%) of 3-(3,5-dimethylbenzoyl)-2'-deoxy-3',5'-di-O-n-pentanoyl-5-fluorouridine were obtained as an oily substance. The physical characteristics of this substance were identical with those of the oily substance obtained in Example 10.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An ester derivative of deoxyfluorouridine of the general formula (I):

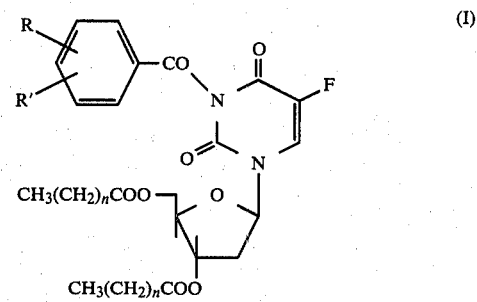

wherein R and R', which may be identical or different, are selected from the group consisting of a hydrogen atom, a halogen atom, and a methyl group and n is 3 or 4.

2. The ester derivative of deoxyfluorouridine according to claim 1, wherein both R and R' are hydrogen atoms.

3. The ester derivative of deoxyfluorouridine according to claim 1, wherein one of R and R' is a hydrogen atom and the other is a methyl group.

4. The ester derivative of deoxyfluorouridine according to claim 1, wherein one of R and R' is a hydrogen atom and the other is a halogen atom.

5. The ester derivative of deoxyfluorouridine according to claim 1, wherein both R and R' are halogen atoms.

6. The ester derivative of deoxyfluorouridine according to claim 1, wherein both R and R' are methyl groups.

7. A pharmaceutical composition containing, as an active ingredient an effective anti-tumor amount of, an ester derivative of deoxyfluorouridine of the general formula:

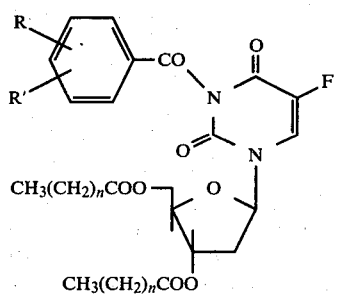

wherein R and R', which may be identical or different, are selected from the group consisting of a hydrogen atom, a halogen atom and a methyl group and n is 3 or 4 and a pharmaceutically acceptable carrier or diluent.

8. A pharmaceutical composition according to claim 7, wherein both R and R' are hydrogen atoms.

9. A pharmaceutical composition according to claim 7, wherein one of R and R' is a hydrogen atom and the other is a methyl group.

10. A pharmaceutical composition according to claim 7, wherein one of R and R' is a hydrogen atom and the other is a halogen atom.

11. A pharmaceutical composition according to claim 7, wherein both R and R' are methyl groups.

12. A pharmaceutical composition according to claim 7, wherein both R and R' are halogen atoms.

13. A pharmaceutical composition according to claim 9 wherein the carrier is polyethylene glycol or cane sugar esters of fatty acids.

* * * * *